United States Patent [19]
Hyldig-Nielsen et al.

[11] Patent Number: 5,612,458
[45] Date of Patent: Mar. 18, 1997

[54] ANTIBODY TO PNA/NUCLEIC ACID COMPLEXES

[75] Inventors: Jens J. Hyldig-Nielsen, Vanløse; Karl-Johan Pluzek, Smoerum, both of Denmark

[73] Assignee: Dako/AS, Denmark

[21] Appl. No.: 361,643

[22] Filed: Dec. 22, 1994

[30] Foreign Application Priority Data

Dec. 23, 1993 [DK] Denmark .................................. 1454/93

[51] Int. Cl.$^6$ .......................... A61K 39/00; A61K 51/10; C07K 16/44
[52] U.S. Cl. .......................... 530/388.21; 435/6; 435/7.1; 435/7.92; 530/387.1; 530/387.3; 530/387.5; 530/389.1; 530/389.3
[58] Field of Search .............................. 435/6, 7.1, 7.92; 530/387.1, 387.3, 387.5, 388.21, 389.1, 389.3

[56] References Cited

U.S. PATENT DOCUMENTS

| | | | |
|---|---|---|---|
| 4,623,627 | 4/1986 | Huang et al. | 435/240 |
| 4,816,567 | 3/1989 | Cabilly et al. | 530/387.1 |
| 4,833,084 | 7/1989 | Carrico | 435/240.27 |

FOREIGN PATENT DOCUMENTS

| | | | |
|---|---|---|---|
| 9201047 | 6/1992 | WIPO | C12N 15/00 |
| 9220702 | 8/1992 | WIPO | C07K 5/00 |
| 9220703 | 11/1992 | WIPO | C07K 5/00 |
| 9312129 | 2/1993 | WIPO | C07H 19/06 |

OTHER PUBLICATIONS

Nielsen et al, Science, 254, 1497–1500 (1991).
Egholm et al, J. Am. Chem. Soc., 114, 9677–9678 (1992).
Buchardt et al, TIBTECH, 11, 384–386 (1993).
Nielsen et al, Bioconjugate Chem., 5, 3–7 (1994).
Moellegaard et al, Proc. Nat. Acad. Sci. USA 91, 3892–3895 (1994).
Egholm et al., "PNA hybridizes to complementary oligonucleotides obeying the Watson–Crick hydrogen–bonding rules", Nature, vol. 365, 566–568 (1993).
"Improved Synthesis, Purification and Characterization of PNA Oligomers", Presented at the 3rd Solid–Phase Symposium, Oxford UK, Aug. 31–Sep. 4, 1994.
Harboe and Ingild, "Immunization isolation of immunoglobulins and antibody titre determination", Scand. J. Immunol., vol. 17, Suppl. 10, 345–351, (1983).
Köhler and Milstein, "Continuous cultures of fused cells secreting antibody of predefined specificity", Nature, 256:495 (1975).
Melchers et al, eds., "Lymphocyte Hybridomas", Springer–Verlag (New York 1978), Preface, IX–XVIII.
Galfré et al., "Preparation of Monoclonal Antibodies: Strategies and Procedures", Methods in Enzymol., vol. 73, part B, 3–46 (1981).
Kennett, R. H., "Fusion protocols" in Monoclonal Antibodies, Plenum Press, pp. 363–375, (1980).
Ørum et al., "Efficient method for constructing comprehensive murine Fab antibody libraries displayed on phage", Nucleic Acids Res, vol. 21, No. 19, 4491–4498 (1993).
Marks et al., "By–passing immunization: Building high affinity human antibodies by chain shufling", Bio/Technology, vol. 10, 779–783 (1992).
Griffiths et al., "Human anti–self antibodies with high specificity from phage display libraries", The EMBO Journal, vol. 12, No. 2, 725–734 (1993).
Waterhouse et al., "Combinatorial infection and in vivo recombination: a strategy for making large phage antibody repertoires", Nucleic Acid Research, vol. 21, No. 9, 2265–2266 (1993).
Gram et al., "In vitro selection and affinity maturation of antibodies from a combinatorial immunoglobulin library", Proc. Natl. Acad. Sci. USA, vol. 89, 3576–3580 (1992).
M. Egholm et al., "Peptide Nucleic Acids (PNA). Oligonucleotide analogues with an achiral peptide backbone", J. Am. Chem. Soc. 114, 1895–1897 (1992).
M. Egholm et al., "Peptide nucleic acids containing adenine or guanine recognize thymine and cytosine in complementary DNA sequences", J. Chem. Soc. Chem. Commun., 800–801 (1993).

*Primary Examiner*—Donald E. Adams
*Attorney, Agent, or Firm*—Graham & James LLP

[57] ABSTRACT

This invention relates to antibodies to complexes formed between PNA (Peptide Nucleic Acid) and nucleic acids, particularly antibodies to PNA/DNA or PNA/RNA complexes. The preferred antibodies are polyclonal, monoclonal and recombinant antibodies that binds to PNA/DNA or PNA/RNA complexes, but not to single-stranded PNA, double-stranded nucleic acid or single-stranded nucleic acid. Peptide Nucleic Acids (PNA) are newly developed, not naturally occurring compounds comprising a polyamide backbone bearing a plurality of ligands such as naturally occuring nucleobases attached to a polyamide backbone through a suitable linker. PNA oligomers with a backbone of N-(2-aminoethyl)glycin units have a surprising high affinity for complementary nucleic acid forming very stable and specific complexes. This property makes PNA oligomers suitable as hybridization probes for detection of nucleic acids. The usability of PNA as hybridization probes is greatly increased by the present antibodies. The antibodies according to the invention are useful in the capture, recognition, detection, identification or quantitation of nucleic acids in biological samples, via their ability to react with PNA-nucleic acid complexes.

21 Claims, No Drawings

ANTIBODY TO PNA/NUCLEIC ACID COMPLEXES

This invention relates to antibodies to complexes formed between PNA (Peptide Nucleic Acid) and nucleic acids Peptide Nucleic Acids (PNA) are newly developed, not naturally occurring compounds comprising a polyamide backbone bearing a plurality of ligands such as naturally occuring nucleobases attached to an amide backbone through a suitable linker. PNA oligomers have a surprising high affinity for complementary nucleic acid forming very stable and specific complexes. This property makes such PNA oligomers suitable as hybridization probes for detection of nucleic acids. The usability of PNA as hybridization probes is greatly increased by the present antibodies.

The antibodies according to the invention are useful in the capture, recognition, detection, identification or quantitation of nucleic acids in biological samples, via their ability to react with PNA-nucleic acid complexes.

BACKGROUND OF THE INVENTION

The capture, recognition, detection, identification or quantitation of one or more chemical or biological entities is useful in the fields of recombinant DNA, human and veterinary medicine, agriculture and food science, among others. In particular, these techniques can be used to detect and identify etiological agents such as bacteria and vira, to screen bacteria for antibiotic resistance, to aid in the diagnosis of genetic disorders and to detect cancerous cells.

The state-of-the-art nucleic acid hybridization assay techniques generally involve hybridization with a labelled form of a complementary polynucleotide probe. Hybridization between particular base sequences or genes of interest in the sample nucleic acid and labelled probe is determined by detection of the labelled hybrids. The preparation of labelled probe generally involves the enzymatic incorporation of radiolabelled or modified nucleotides or chemical Preparation of labelled probes is often time consuming and expensive and has to be carried out without destroying the ability of the probe to detectably hybridize with its complementary Sequence.

Reagents for directly detecting the polynucleotide duplex formed as a result of hybridization between the sample and probe and thereby avoid the chemical labelling of the probes, would overcome this problem.

The generation of specific polyclonal antibodies that will bind double-stranded nucleic acid but not single-stranded nucleic acid is complicated by the fact that polyclonal antisera may contain antibodies that will cross-react with single-stranded nucleic acid. Polyclonal antisera may also contain naturally occuring antibodies to single-stranded nucleic acid or antibodies to single-stranded nucleic acid arising as a result of the immunization.

Monoclonal antibody technology can provide a means to select an antibody with desired affinity and specificity which will overcome the problems discussed above. Such monoclonal antibodies which will selectively bind double-stranded DNA (U.S. Pat. No. 4,623,627) or DNA-RNA hybrids (U.S. Pat. No. 4,833,084) have been prepared and used in the detection of duplexes formed between particular base sequences of interest in the sample nucleic acid and a probe with a known complementary sequence.

A new alternative arising from the construction of the nucleic acid analoque PNA (Peptide Nucleic Acid), is to use a PNA oligomer as a detection probe and generate antibodies that bind to PNA-nucleic acid complexes.

Peptide Nucleic Acids (PNAs) are described in WO 92/20702 as compounds comprising a polyamide backbone bearing a plurality of ligands such as naturally occuring nucleobases attached to a polyamide backbone through a suitable linker. It has recently been shown that PNA in which the backbone is structurally homomorphous with the deoxyribose backbone and consists of N-(2-aminoethyl)glycin units to which the nucleobases are attached can hybridize to complementary oligonucleotides to form PNA-nucleic acid complexes (Egholm et al., Nature, vol 365, 566–568 (1993)).

SUMMARY OF THE INVENTION

One aspect of the present invention is antibodies that binds to complexes formed between PNA and nucleic acids.

Apart from sharing the feature of base pairing, PNA/nucleic acid complexes and nucleic acid duplexes, such as DNA/DNA or DNA/RNA duplexes, possess substantially different properties for example the PNA of a preferred PNA/nucleic acid complex has a backbone consisting of an N-(2-aminoethyl)glycine oligomer or polymer which is achiral and ion charged as opposed to the corresponding strands of an nucleic acid duplex, wherein the backbone is a sequence of nucleotides containing one anion for each phosphate group. The ensuing steric and conformational differences between the two types of compounds makes it absolutely unpredictable whether antibodies binding specifically to PNA/nucleic acid complexes Could be made available.

Other aspects of the invention are antibodies that bind to complexes formed between PNA and DNA or PNA and RNA.

In preferred embodiments the antibodies to complexes formed between PNA and nucleic acids do not bind to single-stranded PNA, double-stranded nucleic acid or single-stranded nucleic acid.

In one of these embodiments the antibody binds to a complex formed between PNA and DNA, but not to PNA/RNA complexes, double-stranded DNA, DNA/RNA hybrids, single-stranded PNA or single-stranded nucleic acid.

In another of these embodiments the antibody binds to a complex formed between PNA and RNA, but riot to PNA/DNA complexes, double-stranded DNA, DNA/RNA hybrids, single-stranded PNA or single-stranded nucleic acid.

Antibodies that bind to PNA/nucleic acid complexes irrespective of the base sequence are also part of the invention.

The invention contemplates polyclonal, monoclonal and recombinant antibodies with binding characteristics as described above.

Polyclonal antibodies of the present invention can be obtained by immunizing a host animal with a complex formed by contacting PNA with nucleic acid, particularly a complex formed between PNA with a backbone of N-(2-aminoethyl)glycin units and DNA or RNA.

Monoclonal antibodies of the present invention can be obtained from a hybridoma prepared by conventional techniques. A selected host animal is immunized with a complex formed by contacting PNA with nucleic acid, lymphocytes from the animal secreting antibodies are fused with myeloma cells to produce hybridomas. Hybridoma cells producing antibodies which bind to PNA-nucleic acid complexes are selected. The selected hybridomas are subcloned to assure monoclonality of the secreted antibody. Preferred complexes for immunization, are complexes formed between PNA with a backbone of N-(2aminoethyl)glycin units and DNA or RNA.

Recombinant antibodies according to the invention can be produced by immunizing a host animal with a PNA/nucleic acid complex, isolating mRNA from antibody producing cells, producing antibody fragment coding cDNA from said mRNA, amplifying said cDNA and inserting it into a phage capable of expressing and displaying the antibody fragments at its surface, infecting bacteria with said phage, selecting the bacteria producing the antibody fragment of interest and using said bacteria for production of the antibody fragments or expressing the antibody fragment coding DNA in another prokaryotic or eukaryotic expression system. Preferred complexes for immunization, are complexes formed between PNA with a backbone of N-(2-aminoethyl)glycin units and DNA or RNA.

Recombinant antibodies of the present invention may also be obtained from large recombinatorial immunoglobulin libraries derived from non-immunized animals and the affinity of the selected antibody binding sites might be increased by chain shuffling or by random mutagenesis.

Various methods for detecting a particular nucleic acid sequence in a test sample are additional aspects of the invention, whereby the antibodies according to the invention are useful in the capture, recognition, detection, identification or quantitation of one or more chemical or biological entities.

The antibodies are very useful in the human and veterinary field. Especially contemplated is the use of the present antibodies to detect the presence or amount of infectious agents in humans such as chlamydial or gonococcal organisms or infections with Epstein-Barr virus or papillomavirus. The present antibodies are also useful in the general field of cytogenetics such as chromosomal painting.

The invention also provides a kit containing antibody according to the invention, which antibody might be in a detectably labelled form, a PNA sequence that is complementary to the nucleic acid sequence to be detected and a detection system.

DESCRIPTION OF THE SPECIFIC EMBODIMENTS

When referring to the antibody of the present invention it is intended to include whole, intact antibodies, antibody fragments, polyfunctional antibody aggregates, or in general any antibody-derived substance that comprises at least one antibody combining site having the characteristics described herein. Antibodies of any of the known classes and subclasses of immunoglobulins are contemplated, e.g., IgG, IgM, and so forth, as well as active fragments such as the Ig fragments conventionally known as scFv, Fab, F(ab'), and F(ab')$_2$.

The term nucleic acid covers a nucleotide polymer composed of subunits, which are either deoxyribonucleosides or ribonucleosides joined together by phosphodiester bridges between the 5'-position of one nucleoside and the 3'-position of another nucleoside. They may be DNA or various types of RNA. The terms bases and nucleobases are used interchangeably for pyrimidine and purine bases of the nucleic acids and PNA.

The PNAs are synthesized according to the procedure described in "Improved Synthesis, Purification and Characterization of PNA Oligomers", Presented at the 3rd Solid-Phase Symposium, Oxford UK, Aug. 31–Sept. 4, 1994.

The PNA-nucleic acid complex used for immunization of an animal according to the present invention may comprise PNA and DNA or RNA. Since both nucleic acid and PNA are devoid of diversed peptide sources, both nucleic acid duplexes and PNA/nucleic acid complexes would be expected to be essentially non-immunogenic in normal host animals (i.e. animal which are not prone to generate autoantibodies against nucleic acid) when injected per se. Whereas in these circumstances the conventional conjugation of the nonimmunogenic antigen to a carrier foreign to the host animal generally has been found to be impractical ahd laborious and furthermore induce a risk of creating structural changes in the antigen, an immune response towards nucleic acid duplexes has been elicited by immunizing normal host animals with non-covalent, ionic complexes formed between the poly-anionic nucleic acid duplex and a poly-cationic protein derivative, particularly a methylated albumin or globulin species (U.S. Pat. No. 4,623,627, U.S. 4,833,084). According to the present invention it has now Surprisingly been found that antibodies against PNA/DNA complexes can be raised by immunizing a normal host animal with a mixture comprising a PNA/DNA complex and a non-derivatized protein heterologous to the host animal, such as ovalbumin. This technology can be applied to immunization with PNA/RNA complexes. Both polyclonal and monoclonal antibodies have been obtained and the technology can be extended to the production of recombinant antibodies.

A PNA-DNA complex can be prepared by contacting double-stranded or single-stranded DNA with a PNA molecule having a base sequence that is complementary to all or part of the DNA sequence, heating the mixture to form single-stranded molecules and allowing the mixture to cool slowly to room temperature. A PNA-RNA complex may be prepared by contacting RNA with a PNA molecule having a base sequence that is complementary to all or part of the RNA sequence, heating the mixture and allowing the mixture to cool slowly to room temperature. A suitable quantity of one of the PNA-nucleic acid complexes is mixed with an adjuvant. The immunogen might be used unconjugated or conjugated to a suitable carrier such as KLH (Keyhole Limpet Hemocyanin), ovalbumin and dextrans.

Polyclonal antibodies of the present invention were obtained by immunizing rabbits with a mixture of a PNA/DNA complex, wherein the PNA had a N-(2aminoethyl)glycin backbone, ovalbumin and a suitable adjuvant. The immunization schedule and bleeding were otherwise performed as described by Harboe and Ingild, Scand. J. Immunol., vol 17, Suppl. 10, 345–351, 1983.

Polyclonal antibodies with a high specificity for PNA/nucleic acid complexes were obtained from the serum of the immunized rabbits. Many animals are suitable as host animals for the production of polyclonal antibodies.

Monoclonal antibodies of the present invention can be harvested from the secretions of hybridoma cells produced by somatic cell hybridization techniques originated from the work of Köhler and Milstein, Nature, 256:495 (1975). The technique is well-known and has undergone various refinements and improvements. Details are described in references such as: Waldmann, M. C. H., "Production of murine monoclonal antibodies," *Monoclonal Antibodies* (ed. P.L.C. Beverly), Churchill Livingston, London, pages 1–20 (1986);

Melchers, F., et al., Preface of "Lymphocyte Hybridoma," *Current Topics In Microbiology and Immunoloqy*, Springer-Verlag, New York, 81: IX–XVIII (1978); Yelton, D. E., et al., "Plasmacytomas and Hybridomas," *Monoclonal Antibodies* (ed. R. H. Kennett, et al.), Plenum Press, New York, pages 3–17 (1980).

Lymphocytes producing antibodies against PNA-nucleic acid complexes may be obtained from various sites, e.g. the lymph nodes, spleen or peripheral blood. The selected lymphocytes are preferably spleen cells from a host animal, e.g. a mouse or a rat, preferably a mouse, which has been immunized with a PNA-nucleic acid complex such as complexes comprising PNA and DNA or RNA. In a preferred embodiment a mouse was immunized intraperitoneally or subcutaneously with a mixture of a PNA/DNA complex, wherein the PNA had a N-(2-aminoethyl)glycin backbone, ovalbumin and a suitable adjuvant.

For fusion myeloma cells of various animal origin can be used, for example, myeloma cells from mice, rats or man. However for reasons of genetic stability it is preferred to fuse lymphocytes and myeloma cells derived from the same animal species and most preferably from the same strain of such animal species. Murine lymphocytes and myeloma cells are most commonly used, preferably from the BALB/c strain, most preferably the myeloma cell line P3-X63-Ag.8.

Fusion of the lymphocyte and myeloma cells to form hybridomas and selection of antibodies according to the invention are accomplished by conventional means. The selected hybridomas as are cultured in vitro for an appropriate length of time and aliquots of the culture fluid are drawn off to provide monoclonal antibody-rich fractions.

Recombinant antibodies of the present invention can be constructed by the antibody-phage technologies described in WO 92/01047 or by Ørum et al., Nucleic Acids Research, vol 21, No 19, 4491–4498 (1993). In short the antibody-phage technology involves the following steps: an animal is immunized with a PNA/nucleic acid complex, such a PNA/DNA or PNA/RNA complex, mRNA is isolated from antibody producing cells, cDNA coding for antibody fragments is produced and amplified, the cDNA is inserted into a phage which expresses and displays the antibody fragment at its surface and which remains intact and infectious. Following infection of bacteria, the bacteria producing the antibody fragment of interest are identified in a screening procedure and used for production of the antibody fragment. The antibody fragment coding DNA might also be transferred to another procaryotic or eucaryotic expression system for expression of the antibody fragment. Recombinant antibodies of the present invention may also be obtained from large recombinatorial immunoglobulin libraries derived from non-immunized animals, e.g. by the methods described by Marks et al., Bio/Technology, Vol. 10, 779–783 (1992), Griffiths et al., The EMBO Journal, Vol. 12, No. 2, 725–734 (1993), Waterhouse et al., Nucleic Acid Research, Vol. 21, No. 9, 2265–2266 (1993) and Gram et al., Proc. Natl. Acad. Sci. USA, Vol. 89, 3576–3580 (1992).

If needed, the specificity and/or affinity of selected recombinant antibodies might be increased by chain shuffling as described in the above identified publication by Marks et al. (1992) or by random mutagenesis as described by Gram et al. (1992) and Griffiths et al. (1993) in the above identified publications.

The antibodies of the present invention are characterized by a high degree of specificity for PNA-nucleic acid, complexes. They do not to any significant degree bind to double-stranded nucleic acid, single-stranded PNA or single-stranded nucleic acid. The specificity of the epitope(s) recognized by the present antibodies appears to be dictated by the conformation of the PNA-nucleic acid complex rather than by any specific sequence of the PNA or the nucleic acid.

As will appear from table 1 the polyclonal antibodies raised against a complex of PNA and a 45-mer DNA reacted strongly with PNA/DNA and PNA/RNA and not with double-stranded DNA, DNA/RNA-hybrids, single-stranded DNA or single-stranded PNA. The antibody reacted strongly with four different PNA/DNA complexes wherein the base sequence was different indicating that the antibody recognizes the conformation of the PNA/DNA complex rather than any specific base sequence in the PNA or DNA.

As will appear from table 2, supernatant from one of the clones, 1G12, obtained from a fusion between spleen cells from a mouse immunized with a complex of PNA and a 45-mer DNA and the myeloma cell line P3-X63-Ag.8 reacted with PNA/DNA complexes irrespective of base sequence, but not with double-stranded DNA, single-stranded DNA or single-stranded PNA. This indicates that the antibody recognizes the conformation of the PNA/DNA complex rather than any specific base sequence in the PNA or DNA.

The supernatant from clone 1B11, which was obtained in the fusion described above, reacted as will appear from table 2 differently in that the reaction appeared to be selective for the PNA/DNA complex used for immunization. Thus at least part of the epitope recognized by this antibody appears to be dictated by the base sequence of the PNA or DNA used for immunization. No significant reaction was seen when testing the supernatant from clone 1 B11 on a PNA/RNA complex, double-stranded DNA, DNA/RNA hybrids, single-stranded PNA or single-stranded RNA.

A high specificity and affinity of the antibodies according to the invention give significant advantages when Used in the isolation, detection and quantitation of PNA-nucleic acid complexes formed between PNA and nucleic acid to be detected in a biological sample. Thus the antibodies with a high specificity for PNA/DNA complexes are particularly valuable in DNA probe based analysis for identifying infectious agents in humans such as chlamydial or gonoccal organims. These antibodies are also very useful in the general field of cytogenetics such as chromosome painting.

Antibodies according to the invention having a high specificity and affinity for PNA/RNA complexes are particularly useful in RNA probe based analysis, for example for identifying mRNA or rRNA sequences specific for particular organisms.

Depending on the particular se of the antibody according to the invention the antibody may be coupled with a detectable label such as enzymatically active groups like coenzymes, enzyme inhibitors and enzymes themselves, fluorescers, chromophores, luminescers, specifically bindable ligands such as biotin or haptens.

The antibodies according to the invention are valuable tools in a number of different methods for detecting a particular nucleic acid sequence, such as a method comprising (a) forming a,complex between the particular nucleic acid sequence to be detected in the sample and a sequence of PNA that is complementary to the nucleic acid sequence to be detected, the complex having at least one epitope for an antibody according to the invention, (b) contacting, any complex that is formed between the PNA sequence and the nucleic acid sequence to be detected with an antibody according to the invention, and (c) determining the presence of antibody-PNA-nucleic acid complexes.

In order to be able to catch the antibody-PNA-nucleic acid complex in (c), the PNA sequence in (a) can be immobilized to a solid phase prior to the contact with the nucleic acid sequence to be detected or the antibody used in (b) can be immobilized to a solid phase prior to contact with the PNA-nucleic acid complex.

If the nucleic acid sequences to be detected exists in an immobilized state in a biological specimen, a method comprising (a) forming al complex between the particular nucleic acid sequence to be detected in the specimen and a sequence of PNA that is complementary to the nucleic acid sequence to be detected, the complex having at least one epitope for an antibody according to the invention, (b) contacting any complex that is formed between the PNA sequence and the nucleic acid sequence to be detected with an antibody according to the invention, and (c) determining the presence of antibody-PNA-nucleic acid complexes, can be used.

In another method the initial step could be an immobilization of the nucleic acid sequence to be detected in a method comprising (a) immobilizing the nucleic acid sequence to be detected to a solid phase, (b) forming a complex between the particular nucleic acid sequence to be detected in the sample and a sequence of PNA that is complementary to the nucleic acid sequence to be detected, the complex having at least one epitope for an antibody according to the invention, (c) contacting any complex that is formed between the PNA sequence and the nucleic acid sequence to be detected with an antibody according to the invention, and (d) determining the presence of antibody-PNA-nucleic acid complexes.

Particularly attractive applications of the present antibodies are described below.

A kit for carrying out the described methods or other methods taking advantage of the antibodies according to the present invention contains in addition to the present antibody in labelled or unlabelled form contain a PNA sequence that is complementary to the nucleotide sequence to be detected, i.e. a PNA probe, and a detection system. The detection system may comprise an enzyme which is able to react with a substrate to form a coloured soluble or insoluble reaction product.

Application 1: Hybridization and detection in solution.

A polynucleotide sequence of interest can be determined in solution by contact with PNA molecules complementary to the sequence of interest followed by contact with an antibody according to the present invention, recognizing the PNA-nucleic acid complexes but not free PNA or nucleic acids. These reactions will result in a large complex which may be detected e.g. in a turbidimetric assay format.

Application 2: Solution hybridization and detection after immobilization.

A polynucleotide sequence of interest can be determined by contacting it with a PNA-oligomer complementary to the sequence of interest. The complexes formed are, while still in solution, contacted with an antibody according to the present invention in a labelled or unlabelled form. The PNA-nucleic acid-antibody complex formed is then captured using e.g. an antibody according to the present invention which has been immobilized on a solid phase. Unbound materials is washed off and the amount of bound PNA-nucleic acid-antibody complex is determined either via the label on the antibody or by using a secondary antibody detection system, provided that the immobilized antibody is derived from an alternative species from that of the detecting antibody.

Alternatively, the PNA-oligomers complementary to the sequence of interest may be labelled with a moiety e.g. biotin, fluorescein, or other haptens which is suitable for catching of PNA-nucleic acid complexes. Unbound materials are washed off and the amount of bound PNA-nucleic acid-antibody complex is determined either via the label on the antibody or by using a secondary antibody detection system.

Application 3: Capture assay

A traditional capture assay consists of the following steps recognition, capture, detection. Such assays may be build up in many different ways. One particular interesting example is outlined below.

An antibody capable of binding a PNA-nucleic acid complex is coupled or otherwise immobilized to a solid support, e.g. an ELISA plate. PNA oligomers and sample are mixed and allowed to react in solution in the wells of the ELISA-plate. If complexes between the PNA and the sample nucleic acids are formed, these complexes are captured by the immobilized antibody. Unbound materials are washed off, and to ensure available binding sites for the detection system other PNA-oligomers capable of binding to the capture material can be added and allowed to react with the bound nucleic acids. An antibody of this invention, e.g. conjugated with an enzyme, is added and allowed to react with the formed PNA-nucleic acid complexes. After washing a suitable enzyme substrate is added and the amount of bound materials is measured.

It may be possible to perform two or more of the steps indicated above simultaneously. Also it may be possible to build either the capture or the detection step based on other recognizable moieties than the PNA-nucleic acid complex indicated above. Such moities could e.g. be biotinylated PNA-oligomers or PNA-oligomers labelled with other haptens, peptides,or polypeptides.

Application 4: Detection of PNA/nucleic acid complexes on solid phase.

Complexes formed between a PNA-oligomer and nucleic acids in which either the PNA or the nucleic acid initially was immobilized on a solid phase can be detected by the antibody of the present invention. This detection can be performed either directly using an antibody conjugated to an enzyme, a fluorescent marker or an other signal generating system, or indirectly using one of the secondary detection systems commonly used for detecting antibodies bound to their target. The solid phase considered should be understood in a very broad sense like e.g. nylon or nitrocellulose membranes (Southern or Northern blots), a tissue section (in situ hybridization), or a plastic surface (an ELISA format).

This system has the advantage that the normally very extensive washing procedures included in these technologies can be reduced to a minimum as unspecific bound PNA-oligomers, being single-stranded, will not give rise to a signal as the antibody only recognizes PNA hybridized to nucleic acids. For the same reason this type of analysis will result in less problems with background caused by unspecific binding of the PNA-oligomer.

Application 5: Biosensor systems

One example of dynamic reaction detection using a biosensor surface is the surface plasmon resonance (SPR) detection system, e.g. employed by the BIAcore biosensor system (Pharmacia). The interaction of biomolecules with an immobilized ligand on a sensor chip is measured at the surface using evanescent light. The system includes a sensor chip to which the ligand can be immobilized in a hydrophilic dextran matrix, a miniaturised fluidics cartridge for the transport of analytes and reagents to the sensor surface, a SPR detector, an autosampler and system control and evaluation software. Specific ligands are covalently immobilized to the sensor chip through amine, thiol or aldehyde chemistry or biospecifically by e.g. biotin—avidin interaction.

The antibody of this invention is coupled to the dextran layer of a sensor chip used in the BIAcore biosensor-system (or other types of biosensor systems). A sample is mixed with a PNA-oligomer and incubated so that a complex is formed between PNA and sample nucleic acids complementary to the PNA-oligomer used. The sample is passed through the flow system of the BIAcore and the antibody coupled to the dextran surface will bind the PNA-nucleic acid complexes if such complexes have been formed. Based on the SPR detection employed by the BIAcore this binding will generate a signal dependent on the amount of materials bound to the surface.

Application 6: Detection of bound PNA in cells.

Under suitable conditions, PNA oligomers may be able to penetrate the cellwall of living or fixed cells, e.g. cell-lines, hemopoetic cells, and animal/human tissues (important in therapeutic applications). It will be important to be able to detect the PNA-oligomers that have reacted with their different targets in the individual cells. Labelling with haptens or other reporter molecules of the PNA-oligomer will not be advantageous as this will inhibit (interfere with) the penetration into the cells. Of great significans is the detection of reacted PNA-oligomers, either by immunohistochemistry (in frozen or fixed tissue biopsies) or by Flow-cytometry (e.g. on cells treated with detergent, acetone or alcohol), or in an in vivo set up to detect binding and/or tissue distribution of PNA's added to a cell culture or administered to a living animal.

The following examples illustrate various aspects of the invention. These examples are not intended to limit the invention in any way.

EXAMPLES

Example 1

Preparation of PNA/DNA complexes. PNA-oligomers, molecules in which the backbone is structurally homomorphous with the deoxyribose backbone of DNA and which consists of N-(2-aminoethyl)glycine units to which nucleobases are attached through a methylenecarbonyl linker, were synthesized and purified as described in "Improved Synthesis, Purification and characterization of PNA Oligomers", presented at the 3rd Solid-Phase Symposium Oxford UK, Aug. 31–Sep. 4, 1994, and by M. Egholm et al., J. Am. Chem. Soc. 114, 1895–1897 (1992) and M. Egholm et al.,J. Chem. Soc. chem. Commun. 800–801 (1993). The base sequence of the PNA used is preferably virtually non-self-complementary in order to avoid self-hybridization in the PNA molecule. The number of purines and pyrimidines is approximately equal to allow information of a double helix configuration rather than a triple helix configuration.

DNA oligomers were synthesized on an abi 381A DNA synthesizer from Applied Biosystems using a standard 381A cycle/procedure. The monomers used were standard β-cyanoethyl phosphoamidites for Applied Biosystems Synthesizer.

The antigen used for immunizing rabbits and mice was made adding one mol of a 45-mer synthetic polydeoxyribonucleotide (DNA) and three mols of a 15-mer PNA oligomer. The 45-mer polydeoxyribonucleotide was designed as three repeated units of 15 nucleotides and the 15-mer PNA oligomer had a base sequence complementary to tile base sequence of the 15-mer unit of the polydeoxyribonucleotide.

The base sequence of the 45-mer polydeoxyribonucleotide was as follows:

5'-GCA AAT GCT CTA GGC GCA AAT GCT CTA GGC GCA AAT GCT CTA GGC-3'.

The base sequence of the 15-mer PNA oligomer was as follows:

H—GCC TAG AGC ATT TGC—$NH_2$

Antigen for immunization of rabbits was prepared by mixing the following in a total volume of 6.01 mL:

106 $OD_{260}$ 45-mer polydeoxyribonucleotide (DNA)

106 $OD_{260}$ 15-mer PNA oligomer 50 mM Tris-HCl, pH 7.5

50 mM NaCl (Note: A ratio of 1 OD DNA to 1 OD PNA is equivalent to a molar ratio of approximately 1:3 using the Same extinction coefficient for DNA and PNA.)

The mixture was heated to 92° C. in a heating block and allowed to cool slowly to room temperature. This solution was evaporated in a vacuum centrifuge and resuspended in 600 μL $H_2O$. Final concentration of PNA/DNA hybrid was approximately 10 mg/mL.

Antigen for immunization of mice was prepared by mixing the following in a total volume of 2 mL:

0.939 mg 45-mer polydeoxyribonucleotide (DNA)

1.145 mg 15-mer PNA oligomer 50 mM Tris-HCl, pH 7.5

50 mM NaCl.

This mixture was heated to 92° C. in a heating block and allowed to cool slowly to room temperature. Final concentration of PNA/DNA hybrid was 1.04 mg/mL.

Complex formation was characterized by electrophoresis of Biotin labelled PNA/DNA complexes in 20% polyacrylamide gels (TBE-buffer, 89 mM Tris-borate, 2 mM EDTA) followed by transfer to a nitrocellulose membrane and visualization using an Alkaline Phosphatase (AP) conjugated Streptavidin complex and the substrate NBT/BCIP.

Example 2

Screening and test systems.

Screening of hybridomas and identification of specific antibody activity were based on results obtained in different ELISA formats. Microtiter plates were coated with streptavidin followed by blocking of excess binding sites. The complexes/compounds used for testing the specificity were labelled with biotin.

PNA oligomers labelled with biotin are produced by using the "solid phase" principle for Boc synthesis. A linker comprising one or two units of 2-(aminoethoxy)ethoxy acetic acid (AEEA) is attached to the PNA oligomer on the resin (see above), and biotin is attached in the following way. Two solutions were used. The first solution contained 0.1M biotin in 5% s-collidin in DMF with 2 equivalents of N-ethyldicyclohexylamine and the second solution contained 0.18M HBTU (2-( 1H-benzotriazole-1-yl)-1,1,3,3-tetramethyluronium hexafluorophosphate) in DMF. The two solutions were mixed in a ratio of 2 to 1 and the mixture was left for approximately one minute before it was combined with the resin to which the PNA oligomer with one or two units of AEEA was attached.

For biotin labelling of DNA the following two procedures were used. For labelling in the 5' end of the DNA oligomers a spacer (Spacer phosphoramidite, Clontech Laboratories) was connected to the 5'-OH of the oligomer and then reacted with a biotin labelling reagent (Biotin CE phosphoramidite, 22-0001-35, Cruachem Limited). For labelling in the 3' end of the oligomers the DNA synthesis was started from a Biotin-CPG support (3'-Biotin-ON CPG cat #RP-5225-2 K. J. Ross Petersen, Agern Alle 3, DK-2970 Hørsholm). The first reagent was a spacer (Spacer phosphoamidite, Clontech Laboratories, Inc.) and the monomer reagents were added for synthesising the oligomer.

RNA oligomers were purchased from "DNA Technology Aps, Science Park Aarhus, Gustav Wieds vej 10, DK-8000 Aarhus.

The following detection systems were used:
1. layer: streptavidin
2. layer: 100 ng/mL of biotinylated test complex/compound
3. layer: dilution of antibody according to the invention (polyclonal, monoclonal or recombinant)
4. layer: anti rabbit or anti mouse antibodies conjugated with HRP (Horseradish peroxidase)

Substrate: OPD (o-phenylenediamine)

The following test complexes/compounds were used:
A. A PNA/DNA complex comprising 45-mer DNA and 3 units of 15-mer PNA having the same base sequence as the complex used for immunization and wherein biotin is attached to the 3' end of the DNA as described above.
B. A single stranded 15-mer DNA (ssDNA) corresponding to one of the three 15 nucleotide long sequences of the 45-mer DNA in the complex used for immunization and labelled with biotin at the 5' end as described above.
C. A single stranded 15-mer PNA (ssPNA) with a base sequence corresponding to the 15-mer PNA in the complex used for immunization and labelled with biotin in 5' end as described above.
D. A PNA/DNA complex comprising a 20-mer PNA and a 20-mer DNA having a base sequence that is different from the sequence of the complex used for immunization and wherein the PNA is labelled with biotin at the 5' end as described above. The following sequence was used:

PNA: 5'-Bio-AEEA—AEEA—CGG—CCG—CCG—ATA—TTG—GCA—AC—NH$_2$-3'
DNA: 5'-GTT—GCC—AAT—ATC—GGC—GGC—CG-3'

E. A single stranded 15-mer PNA (ssPNA) with a base sequence as described in D, i.e. different from the base sequence used for immunization.

F. A PNA/DNA complex comprising a 17-mer PNA and DNA wherein the base sequence is different from the sequence of PNA/DNA in A and D and wherein the complexes were labelled with biotin either at the 5' end of the DNA (F1) or at the 5' end of the PNA (F2). The following sequences were used:

F1:

DNA: 5'-Bio-spacer-ATT—GTT—TCG—GCA—ATT—GT-3'
PNA: 5'-H—AEEA—ACA—ATT—GCC—GAA—ACA—AT—NH$_2$-3'

F2:

DNA: 5'-ATT—GTT—TCG—GCA—ATT—GT-3'
PNA: 5'-Bio-AEEA—ACA—ATT—GCC—GAA—ACA—AT—NH$_2$-3'

G. Single stranded PNA with the base sequence described in F2 above.
H. Single stranded DNA with the base sequence described in F1 above.
I. A PNA/RNA complex comprising a 19-mer PNA and a 19-mer RNA with a base sequence complementary to the PNA base sequence.
J. Double stranded DNA comprising fragments of calf thymus DNA (Sigma D-1501; converted to fragments comprising from 200 to 1000 bp).
K. A RNA/DNA duplex comprising the 19-mer RNA in I and the complementary DNA sequence.

Example 3

Production of polyclonal antibodies.

To approximately 5 mg of the PNA/DNA antigen described in example 1 (final concentration approximately 10 mg/mL) was added 0.1 mL ovalbumin solution (10 mg Sigma A-7641 lot 70H8210 per mL of 0.1M NaCl, 0.015M NaN$_3$) and 0.01 mL 1.5M NaN$_3$ and this mixture was stepwise whirl mixed into 0.5 mL Titermax #R1 adjuvant (Vaxcel Inc., Norcross, GA. USA). Before immunization the volume of this immunization composition was either 1 mL (the first four immunizations) or adjusted to 2 mL (the following immunizations) by addition and mixing with 0.1M NaCl, 0.015M NaN$_3$.

Five rabbits were each immunized subcutaneously with a dose of approximately 0.5 mg PNA/DNA (total) per immunization, by injecting a volume of 0.1 mL immunization composition for the first four immunizations and 0.2 mL for the following immunizations. Blood samples were taken before immunization and samples for analysis of antibody activity were taken 8 and 10 weeks after the first immunization. The immunization schedule and bleeding were as described in Harboe and Ingild A, Scand. J. Immunol., vol 17, Suppl. 10, 345–351, 1983.

Sera taken before immunization and 10 weeks after immunization of five rabbits were analyzed in the test systems described in example 2. The sera were diluted 2 fold starting at 1:250 (1:250, 1:500, 1:1000, 1:2000, 1:4000, 1:8000, 1:16000, 1:32000) and horseradish peroxidase conjugated swine anti rabbit immunoglobulin was used for visualization. In table 1 the results from one representative experiment is shown. The optical density at 492 nm gained by diluting the antibodies 1:500 is shown in tests of sera using the test complexes/compounds A, B, C, D, E, F, H, I, J, and K described in example 2.

TABLE 1

| Test complex/ compounds | Serum taken before immunization | Serum taken 10 weeks after first immunization. |
|---|---|---|
| A (PNA/DNA) | 0.257 | >3.0 |
| B (DNA) | 0.155 | 0.437 |
| C (PNA) | 0.179 | 0.317 |
| D (PNA/DNA) | 0.115 | 2.467 |
| E (PNA) | 0.248 | 0.649 |
| F1 (PNA/DNA) | 0.200 | 2.751 |
| F2 (PNA/DNA) | 0.205 | 2.456 |
| H (DNA) | 0.088 | 0.133 |
| I (PNA/RNA) | 0.139 | 2.011 |
| J (dsDNA) | 0.129 | 0.086 |
| K (RNA/DNA) | 0.106 | 0.107 |

As shown in table 1, serum taken from the bleeding 10 weeks after immunization strongly reacted with the PNA/DNA complexes (A, D, F1 and F2) and the PNA/RNA complex (I), whereas no significant reaction was seen using the serum taken before immunization. Dose response curves were obtained when testing the dilutions of the serum 10 weeks after immunization using these antigens. No significant reaction was seen when testing the sera on double-stranded DNA, RNA/DNA duplexes, single-stranded PNA or DNA. Sera was also testet in a filter dot assay using the test complexes/compounds A,I and K described in example 2 and the individual PNA, DNA and RNA strands of these complexes. The test compounds were dotted in amounts of 20, 10, 5 or 2.5 ng on filters, followed by sera diluted 1:2000 in 0.5% casein in TS-buffer (50 mM Tris-HCl, 500 mM NaCl, pH 9.0) and the antibody captured by the test compounds on the filters was visualized with alkaline phosphatase conjugated goat anti rabbit Ig. Only positive reaction was seen with the PNA/DNA complex (A) in example 2 at a detection limit of 5 ng.

Sera was tested in a Southern blot format. Three sets of four different DNA oligonucleotides were loaded on a denaturing 20% polyacrylamide gel. Two of the DNA oligonucleotides used are as described in A and F 1 in example 2 and the other two were unrelated DNA oligomers. After electrophoresis the DNA oligonucleotides were transferred to Nytran, nitrocellulose membranes. One filter was hybridized with the PNA oligomer described in A (from example 2), one filter with the PNA oligomer described in F1 (example 2) and the last filter with a mixture of these two PNA oligomers. After blocking unreacted sites, the membranes were incubated 2 hours at 30° C. with the polyclonal antibody according to the invention (diluted 1:2000). Bound antibody was visualized using alkaline phosphatase conjugated goat anti rabbit Ig and the substrate NBT/BCIP. Only the lanes containing DNA oligonucleotides complementary to the PNA oligomer used for hybridization gave rise to a band with a position as expected for the size of the DNA oligonucleotides used. Thus the polyclonal antibody according to the invention recognizes the PNA/DNA complexes formed in a Southern blot on the nitrocellulose membranes.

Example 4

Production of monoclonal antibodies. The PNA/DNA antigen prepared as described in example 1 was at a concentration of 1.04 mg/mL mixed with ovalbumin to a concentration of ovalbumin of 250 µg/mL. 0.1 mL of this mixture and 0.1 mL Freunds incomplete adjuvant was used for immunizing female Balb/c mice intraperitoneally or subcutaneously five times with an interval of approximately three weeks. Three days before the fusion Was planned a mouse was immunized intraperitoneally without adding adjuvant to tile mixture of PNA/DNA antigen and ovalbumin. The fusion was carried out using standard fusion procedure with spleen cells from the immunized mouse and the myeloma cell line P3-X63-Ag.8 as fusion partner.

Initial screening took place 14 days after the fusion and 50 clones were selected as given a positive signal in an ELISA system as described in example 2 using test complex A in the; second layer. Positive clones were cultivated and supernatants were retested in the ELISA systems described in example 2 using test complexes/compounds A, B and C. Clonality was ensured by limited dilution of the cells followed by screening of the supernatants in ELISA. Hybridomas were grown under standard conditions in RPMI 1640 medium supplemented with 10% foetal calf serum.

The supernatants were tested in the test systems described in example 2. The supernatant from two clones (1G12 and 1B11) showed preferential binding to PNA/DNA complexes as shown in table 2. The supernatants were diluted 2 fold as follows 1:2, 1:4, 1:8, 1:16, 1:32, 1:64 and 1:128. Horseradish peroxidase conjugated anti mouse immunoglobulin was used for visualization. In table 2 the results from one representative experiment is shown. The optical density at 492 nm gained by diluting the supernatant 1:2 is shown in tests of sera using the test complexes/compounds A, B, C, D, E, F, G, H, I, J and K described in example 2.

TABLE 2

| Test complexes/compounds | supernatant from clone 1G12 | Supernatant from clone 1B11 |
|---|---|---|
| A (PNA/DNA) | 1.521 | 1.055 |
| B (DNA) | 0.061 | 0.024 |
| C (PNA) | 0.111 | 0.038 |
| D (PNA/DNA) | 1.805 | 0.234 |
| E (PNA) | 0.110 | 0.147 |
| F1 (PNA/DNA) | 1.136 | 0.106 |
| F2 (PNA/DNA) | 0.517 | 0.147 |
| G (PNA) | 0.146 | 0.134 |
| H (DNA) | 0.075 | 0.081 |
| 1 (PNA/RNA) | not tested | 0.112 |
| J (dsDNA) | 0.097 | 0.106 |
| K (RNA/DNA) | not tested | 0.042 |

As shown in table 2, supernatant from clone 1G12 reacted with the PNA/DNA complexes A, D, F1 and F2. Dose response curves were obtained when testing dilutions of the supernatant. No significant reactions were seen when testing the supernatant on any of the other mentioned test compounds. The supernatant from clone 1B11 reacted differently from the supernatant from clone 1G12 in that the reactivity appeared to be directed primarily towards the PNA/DNA used for immunization (A).

The immunoglobulin class of the supernatants were tested in standard ELISA system for determination of the Ig class. The antibodies from both clones were found to be of the IgM type.

Example 5

Production of recombinant antibody.

Recombinant antibodies according to the invention can be produced by immunizing a mouse as described in example 4, isolating mRNA from antibody producing cells, producing antibody fragment coding cDNA from said mRNA, amplifying said cDNA and inserting it into a phage capable of expressing and displaying the antibody fragments at its surface, infecting bacteria with said phage, selecting the bacteria producing the antibody fragment of interest and using said bacteria for production of the antibody fragments or expressing the antibody fragment coding DNA in another prokaryotic or eukaryotic expression system.

Example 6

Recombinant antibodies of the present invention may also be obtained from large recombinatorial immunoglobulin libraries derived from non-immunized animals, e.g. by the methods described by Marks et al., Bio/Technology, Vol. 10, 779–783 (1992), Griffiths et al., The EMBO Journal, Vol. 12, No. 2, 725–734 (1993), Waterhouse et al. Nucleic Acid Research, Vol. 21, No. 9, 2265–2266 (1993) and Gram et al., proc. Natl. Acad. Sci. USA, Vol. 89, 3576–3580 (1992). The affinity of the selected antibody binding sites might be increased by chain shufling as described in the above identified publication by Marks et al. (1992) or by random mutagenesis as described by Gram et al. (1992) and Griffiths et al. (1993) in the above identified publications.

Although PNA comprising a N-(2-aminoethyl)glycin backbone has been used in the present work, this should not be taken as a limitation. It is expected that PNA with other types of backbone can be used in a similar way as long as the PNA is capable of forming stable complexes with nucleic acids.

Modification of the above described modes for carrying out the invention that will be clear to those skilled in the fields of immunochemistry, nucleic acid chemistry and related fields are intended to be within the scope of the following claims.

We claim:

1. Antibody characterized in that it binds to complexes formed between PNA (Peptide Nucleic Acid) and nucleic acids.

2. Antibody according to claim 1, characterized in that it does not bind to single-stranded PNA, double-stranded nucleic acid, or single-stranded nucleic acid.

3. Antibody according to claim 1 or 2, characterized in that it is polyclonal.

4. Antibody according to claim 3, characterized in that it binds to a complex formed between PNA and DNA, but not to PNA/RNA complexes, double-stranded DNA, DNA/RNA-hybrids, single-stranded PNA or single-stranded DNA.

5. Antibody according to claim 3, characterized in that it is obtainable by immunizing a host animal with a complex formed between PNA with a N-(2-aminoethyl)glycin backbone and DNA.

6. Antibody according to claim 5, characterized in that it binds to PNA/ DNA complexes irrespective of the base sequence.

7. Antibody according to claim 3, characterized in that it is obtainable by immunizing a host animal with a complex formed between PNA with a N-(2-aminoethyl)glycin backbone and RNA.

8. Antibody according to claim 1 or 2, characterized in that the antibody is monoclonal.

9. Antibody according to claim 8, characterized in that it binds to a complex formed between PNA and DNA, but not to PNA/RNA complexes, double-stranded DNA, DNA/RNA hybrids, single-stranded PNA or single-stranded DNA.

10. Antibody according to claim 8, characterized in that it is obtainable by immunizing a host animal with a PNA/DNA-complex, wherein the PNA has a backbone of N-(2-aminoethyl)glycin, fusing antibody producing cells from said animal with neoplastic cells to produce hybridomas and selecting hybridomas at produce an antibody that binds to complexes formed between PNA and nucleic acids.

11. Antibody according to claim 8, characterized in that it is obtainable by immunizing a host animal with a PNA/RNA-complex, wherein the PNA has a backbone of N-(2-aminoethyl)glycin, fusing antibody producing cells from said animal with neoplastic cells to produce hybridomas and selecting hybridomas that produce an antibody that binds to complexes formed between PNA and nucleic acids.

12. Antibody according to claim 1 or 2, characterized in that the antibody is recombinant.

13. Antibody according to claim 1 in detectably labelled form.

14. A method for detecting a particular nucleic acid sequence in a test sample, comprising (a) forming a Complex between the particular nucleic acid sequence to be detected in the sample and a sequence of PNA that is complementary to the nucleic acid sequence to be detected, the complex having at least one epitope for an antibody according to claim 1, (b) contacting any complex that is formed between the PNA sequence and the nucleic acid sequence to be detected with an antibody according to claim 1, and (c) determining the presence of antibody-PNA-nucleic acid complexes.

15. A method according to claim 14, characterized in that the antibody used in (b) is immobilized to a solid phase prior to contact with the PNA-nucleic acid complex.

16. A method according to claim 14, characterized in that the PNA sequence in (a) is immobilized, to a solid phase prior to the contact with the nucleic acid sequence to be detected.

17. A method for detecting a particular nucleic acid sequence which exists in an immobilized state in a biological specimen, comprising (a) forming a complex between the particular nucleic acid sequence to be detected in the specimen and a sequence of PNA that is complementary to the nucleic acid sequence to be detected, the complex having at least one epitope for an antibody according to claim 1, (b) contacting any complex that is formed between the PNA sequence and the nucleic acid sequence to be detected with an antibody according to claim 1, and (c) determining the presence of antibody-PNA-nucleic acid complexes.

18. A method for detecting a particular nucleic acid sequence in a test sample, comprising (a) immobilizing the nucleic acid sequence to be detected to a solid phase, (b) forming a complex between the particular nucleic acid sequence to be detected in the sample and a sequence of PNA that is complementary to the nucleic acid sequence to be detected, the complex having at least one epitope for an antibody according to claim 1, (c) contacting any complex that is formed between the PNA sequence and the nucleic acid sequence to be detected with an antibody according to claim 1, and (d) determining the presence of antibody-PNA-nucleic acid complexes.

19. A kit for detecting a particular nucleic acid sequence in a sample, said kit containing an antibody according to claim 1, a PNA sequence that is complementary to the nucleic acid sequence to be detected and a second antibody conjugated to an enzyme or a fluorescent marker.

20. A kit or detecting a particular nucleic acid sequence in a sample, said kit containing an antibody in a detectably labelled form according to claim 13 and a PNA sequence that is complementary to the nucleic acid sequence to be detected.

21. A kit for detecting a particular nucleic acid sequence in a sample, said kit containing an antibody according to claim 1 and a labelled PNA sequence that is complementary to the nucleic acid sequence to be detected.

* * * * *